US009282295B2

(12) United States Patent
Papalazarou et al.

(10) Patent No.: US 9,282,295 B2
(45) Date of Patent: Mar. 8, 2016

(54) IMAGING APPARATUS FOR IMAGING AN OBJECT

(75) Inventors: Chrysi Papalazarou, Eindhoven (NL); Peter Maria Johannes Rongen, Eindhoven (NL); Peter Hendrik Nelis De With, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 244 days.

(21) Appl. No.: 13/882,512

(22) PCT Filed: Nov. 2, 2011

(86) PCT No.: PCT/IB2011/054860
§ 371 (c)(1),
(2), (4) Date: Apr. 30, 2013

(87) PCT Pub. No.: WO2012/059867
PCT Pub. Date: May 10, 2012

(65) Prior Publication Data
US 2013/0215249 A1    Aug. 22, 2013

(30) Foreign Application Priority Data

Nov. 5, 2010 (EP) .................................... 10190095

(51) Int. Cl.
*H04N 9/47* (2006.01)
*H04N 7/18* (2006.01)
(Continued)

(52) U.S. Cl.
CPC .. *H04N 7/18* (2013.01); *A61B 6/02* (2013.01); *A61B 6/4435* (2013.01); *A61B 6/461* (2013.01);
(Continued)

(58) Field of Classification Search
USPC .............. 348/77, 45, 44, 42, 136, 333.1, 744; 345/419, 652, 663, 664, 665, 666, 675; 600/415, 424, 427, 429, 433, 434, 435, 600/466; 606/130; 700/59, 245, 250
See application file for complete search history.

(56) References Cited

U.S. PATENT DOCUMENTS 8,010,181 B2 *   8/2011   Smith et al. ................... 600/424
8,146,874 B2 *   4/2012   Yu ............................... 248/316.1
(Continued)

FOREIGN PATENT DOCUMENTS

WO        2005044125 A1    5/2005
WO        WO2008078259     7/2008
(Continued)

OTHER PUBLICATIONS

R. Hartley et al., "Multiple View Geometry in Computer Vision", Second Edition, Cambridge University Press, pp. 1-9, 2003.
(Continued)

*Primary Examiner* — Jefferey Harold
*Assistant Examiner* — Mustafizur Rahman

(57) ABSTRACT

The invention relates to an imaging apparatus for imaging an object (3) being preferentially a catheter. A kinematics model (12) of a robot representing the object (3), which is defined by kinematics parameters, and projection data of the object (3), which correspond to different projection directions, are provided. The kinematics model (12) is modified by modifying the kinematics parameters such that a difference between simulated projection data, which are determined by simulating a forward projection of the kinematics model (12), and the provided projection data is minimized. Since the object (3) is represented by a kinematics model (12) of a robot, movements of the object (3), in particular, deformations of the object (3), can be described in a simple way by few kinematics parameters, thereby allowing modifying the model (12) and, thus, following a movement of the object fast by modifying the few kinematics parameters, in particular, in real-time.

12 Claims, 3 Drawing Sheets

(51) Int. Cl.
*A61B 6/02* (2006.01)
*A61B 6/00* (2006.01)
*A61B 19/00* (2006.01)

(52) U.S. Cl.
CPC ............... *A61B 6/486* (2013.01); *A61B 19/50* (2013.01); *A61B 2019/502* (2013.01); *Y10S 901/46* (2013.01)

(56) References Cited

U.S. PATENT DOCUMENTS

| | | | |
|---|---|---|---|
| 8,219,177 B2* | 7/2012 | Smith et al. | 600/424 |
| 8,219,178 B2* | 7/2012 | Smith et al. | 600/424 |
| 8,290,571 B2* | 10/2012 | Younge et al. | 600/424 |
| 8,391,957 B2* | 3/2013 | Carlson et al. | 600/429 |
| 2001/0034480 A1 | 10/2001 | Rasche et al. | |
| 2004/0149036 A1 | 8/2004 | Foxlin | |
| 2005/0073585 A1* | 4/2005 | Ettinger et al. | 348/155 |
| 2006/0025893 A1 | 2/2006 | Fischer et al. | |
| 2006/0079745 A1 | 4/2006 | Viswanathan | |
| 2006/0200026 A1 | 9/2006 | Wallace et al. | |
| 2006/0258938 A1 | 11/2006 | Hoffman et al. | |
| 2007/0016067 A1 | 1/2007 | Webster et al. | |
| 2007/0197896 A1* | 8/2007 | Moll et al. | 600/407 |
| 2007/0232897 A1 | 10/2007 | Horndler et al. | |
| 2009/0012533 A1* | 1/2009 | Barbagli et al. | 606/130 |
| 2009/0014986 A1 | 1/2009 | Chen et al. | |
| 2009/0088634 A1* | 4/2009 | Zhao et al. | 600/427 |
| 2009/0088773 A1* | 4/2009 | Zhao et al. | 606/130 |
| 2009/0088897 A1* | 4/2009 | Zhao et al. | 700/250 |
| 2009/0149867 A1 | 6/2009 | Glozman et al. | |

FOREIGN PATENT DOCUMENTS

| | | |
|---|---|---|
| WO | 2009118671 A1 | 10/2009 |
| WO | WO2009118671 | 10/2009 |

OTHER PUBLICATIONS

P. Corke, "A Robotics Toolbox for MATLAB", IEEE Robotics & Automation Magazine, Mar. 1996, pp. 24-32.

B. Siciliano et al., "Robotics Modelling, Planning and Control", Advanced Textbooks in Control and Signal Process, pp. 58-65, 2008.

C. Papalazarou et al., "Surgical Needle Reconstruction Using Small-Angle Multi-View X-Ray", Eindhoven University of Technology, Eindhoven, The Netherlands, 2009.

Chrysi Papalazarou et al, "Catheter reconstruction in multi-view X-ray using Non-Rigid Structure-from-Motion and a Robotics model", University of Technology Eindhoven. Feb. 23, 2012.

* cited by examiner

| L | a | α | d | θ | |
|---|---|---|---|---|---|
| 1 | 0 | 0 | $d_1$ | 0 | $d_1$ |
| 2 | 0 | $\pi/2$ | 0 | $\theta_2$ | $\theta_2$ |
| 3 | 0 | $\pi/2$ | 0 | $\pi/2+\theta_3$ | $\theta_3$ |
| 4 | 0 | $\pi/2$ | $d_4$ | 0 | $d_4$ |
| 5 | 0 | $\pi/2$ | 0 | $\pi+\theta_5$ | $\theta_5$ |
| 6 | 0 | $\pi/2$ | 0 | $\theta_6$ | $\theta_6$ |
| 7 | 0 | 0 | $d_7$ | 0 | - |

IMAGING APPARATUS FOR IMAGING AN OBJECT

FIELD OF THE INVENTION

The invention relates to an imaging apparatus, an imaging method and an imaging computer program for imaging an object.

BACKGROUND OF THE INVENTION

The article "Surgical needle reconstruction using small-angle multi-view X-ray" by C. Papalazarou et al., Proceedings of the 17th International Conference on Image Processing (ICIP), IEEE, September 2010 discloses a method for reconstructing surgical needles using multi-view x-ray imaging with a small motion of a C-arm. The extend of the motion is limited to an angular range of less than 30 degrees. This small motion provides sufficient multi-view information, which is used in combination with a needle model for a three-dimensional reconstruction of the needle. This method allows reconstructing a three-dimensional image of the needle, if the needle remains static among different views. However, if the needle moves, in particular, is deformed, during the different views, a three-dimensional image of the needle having a good quality cannot reliably be reconstructed.

SUMMARY OF THE INVENTION

It is an object of the present invention to provide an imaging apparatus, an imaging method and an imaging computer program for imaging an object, which allow reliably generating a good quality image, even if the object moves, in particular, even if the object is deformed.

In a first aspect of the present invention an imaging apparatus for imaging an object is presented, wherein the imaging apparatus comprises:
 a model providing unit for providing a kinematics model of a robot representing the object, wherein the kinematics model is defined by kinematics parameters,
 a projection data providing unit for providing projection data of the object, which correspond to different projection directions,
 a model modification unit for modifying the kinematics model by modifying the kinematics parameters such that a difference between simulated projection data, which are determined by simulating a forward projection of the kinematics model, and the provided projection data is minimized.

Since the object is represented by a kinematics model of a robot, movements of the object, in particular, deformations of the object, can simply be described by relatively few kinematics parameters. The model can therefore be relatively fast modified by modifying the few kinematics parameters. Movements of the object can therefore be followed fast, in particular, in real-time, by modifying the few kinematics parameters and, thus, the kinematics model such that a difference between simulated projection data, which are determined by simulating a forward projection of the modified kinematics model, and the provided projection data is minimized, wherein the modified kinematics model represents an image and can completely or partly be shown on, for example, a display. A good quality image of the object can therefore be provided, even if the object moves, in particular, even if the object is deformed.

The kinematics model is preferentially a model of a continuum robot. A robot can be defined as, for example, a mechanical model of a manipulator comprising a set of bodies, called links, in a chain, connected by joints. Each joint can have one degree of freedom, either translational or rotational. For a robot with n joints numbered from 1 to n, there can be n+1 links, numbered from 0 to n. A continuum robot is preferentially a robot that can bend smoothly along its entire length, where the transitions between links are continuous and not sharp. Such a continuum robot of the object can be expressed in terms of the kinematics model.

The kinematics model is a model of the robot, which can be used for describing kinematics of the robot, in particular, a deformation of the robot, by defining the kinematics parameters. A kinematics parameter describes, for example, a rotation or a translation of a part of the kinematics model of the object with respect to another part of the kinematics model of the object.

The object is preferentially a catheter, in particular, a bidirectional catheter, which has been introduced into a person or an animal, wherein the imaging apparatus is adapted to provide an image of the catheter within the person or the animal by providing the modified kinematics model.

Preferentially, the projection data of the object correspond to different projection directions and have been acquired over time such that, if the object has moved, projection data which correspond to different projection directions correspond to the object at another location and/or in another deformed condition. This movement and/or deformation of the object can be followed by modifying the few kinematics parameters such that the difference between the simulated projection data, which are determined by simulating a forward projection of the kinematics model, and the provided projection data is minimized.

It is preferred that the projection data providing unit is adapted to provide projection data which correspond to a wiggling of the projection direction. Since the projection data providing unit is preferentially adapted to provide projection data which correspond to a wiggling of the projection direction, and since the object is imaged by generating the modified kinematics model, which is modified based on the provided projection data, an image of the object, i.e. a three-dimensional representation, can be generated, although projection data have been acquired only over a very limited angular range which may be smaller than 30 degrees. It is therefore not necessary to acquire projection data over an angular range of at least 180 degrees as required by, for example, computed tomography methods.

The projection data providing unit can be a storage unit, in which projection data, which correspond to different projection directions, are stored already, or it can be a projection acquisition unit for acquiring the projection data in the different projection directions, i.e. for acquiring different views. The projection acquisition unit preferentially comprises a radiation source for emitting radiation for traversing the object and a detection unit for detecting the radiation after having traversed the object and for generating the projection data depending on the detected radiation. In particular, the radiation source is an x-ray source and the detection unit is an x-ray detector. The radiation source and the detection unit can be mounted on a C-arm. However, also other kinds of radiation sources and corresponding detection units can be used for generating the projection data. For example, the radiation source can be adapted to emit nuclear radiation, which traverses the object, and which is detected by a corresponding detection unit. Moreover, the radiation source and the detection unit can also be mounted on another device not being a C-arm.

The provided projection data which correspond to a wiggling of the projection direction has preferentially been acquired by using a radiation source and a detection unit. The wiggling is preferentially performed by rotating the radiation source and the detection unit around a rotational axis such that an imaginary axis connecting the radiation source and the detection unit traces a surface of an imaginary cone. The imaginary cone has its apex preferentially at the isocenter of the rotation, wherein the isocenter is a point that the imaginary axis always intersects, regardless of the rotational movement of the radiation source and detection unit, which may be mounted to a same gantry. The base of the cone may in general have any planar shape. Preferably it is a closed curve, and it can be a smooth curve. A closed curve has the advantage that it is easy to make the movement periodic. The closed curve is, for example, a circle or an ellipse. A smooth curve has the advantage that it is easier to control the movement and makes the acquisition more stable and less noisy. Alternatively, the base of the curve forms a linear shape, in which case the radiation source and the detection unit can move linearly and preferably repeatedly between two end positions. The projection data, i.e. a series of two-dimensional projection images, has preferentially been acquired during the wiggling motion of the radiation source and the detection unit.

It is preferred that the projection data represent projections generated by using a projection acquisition unit, wherein a calibration of the projection acquisition unit is defined by calibration parameters, and wherein the model modification unit is adapted to modify the calibration parameters and the kinematics parameters such that a difference between simulated projection data, which are determined by simulating a forward projection of the model, and the provided projection data is minimized. The calibration parameters preferentially define which projection data value detected by the detection unit corresponds to which beam direction, i.e. corresponds to which direction along the beam has travelled, which has met the detection unit at a respective detection location at which the respective projection data value has been detected. The calibration parameters describe therefore preferably the projection geometry. The calibration parameters can be, for example, intrinsic calibration parameters or extrinsic calibration parameters. Intrinsic calibration parameters are, for example, those related to the detection unit itself like a detector pixel size, while extrinsic parameters are those related to the position of the detection unit and radiation source in the world, in particular, the rotational and translational position of the detection unit and radiation source. Since the model modification unit can be adapted to also modify one or several calibration parameters, in addition to modifying the kinematic parameters, such that a difference between simulated projection data, which are determined by simulating a forward projection of the model, and the provided projection data is minimized, the model can be modified, in order to follow a movement of the object, in particular, in order to follow a deformation of the object. A good quality image, i.e. a three-dimensional representation, of the object can therefore be provided, even if one or several calibration parameters are not reliable.

In a further preferred embodiment, the calibration parameters are not modified, in particular, the kinematics model is modified by only modifying the kinematic parameters. The calibration parameters can therefore be considered as being known and fixed, i.e. the projection geometry can be considered as being known. Projection acquisition units like an x-ray C-arm are generally calibrated regularly and are generally designed to be very repeatable, thus making both, intrinsic and extrinsic parameters, reliable. Thus, if the calibration parameters can be considered as being known and fixed, the kinematics model can be modified by modifying the kinematics parameters, without modifying the calibration parameters, thereby reducing the parameter space and allowing modifying the model faster and, in particular, more accurately.

It is further preferred that the kinematics model comprises a series of rigid links connected by joints, wherein each joint describes either a three-dimensional rotation around an axis or a translation along the axis. The respective joint is therefore either a revolute joint or a prismatic joint. Each joint can therefore be controlled by a rotation angle or a translation distance. The kinematics model is preferentially defined by a succession of these joints. In an embodiment, the object is a catheter and the kinematics model models the catheter as a succession of the joints and links. The model providing unit is preferentially adapted to represent the pose of a joint by four kinematics parameters in the Denavit-Hartenberg (D-H) convention. In particular, the pose of each joint is represented by four kinematics parameters in the D-H convention. The pose defines preferentially the location and the orientation of the respective joint. The D-H convention allows representing the kinematics model with a minimal set of parameters.

It is preferred that the object is a catheter and the kinematics model comprises seven joints which are controlled by three kinematics parameters, wherein the model modification unit is adapted to modify the model by modifying the three kinematics parameters. Since the kinematics model can be modified by just modifying three kinematics parameters, the kinematics model can follow movements and/or deformations of the catheter even faster, thereby further improving the quality of providing an image of a moving and/or deforming catheter.

It is further preferred that the model modification unit is adapted to
  determine a two-dimensional track of projections of the object in the provided projection data,
  determine the simulated projection data such that the simulated projection data define a simulated two-dimensional track,
  modify the model such that a difference between the determined two-dimensional track and the simulated two-dimensional track is minimized. This difference between the determined two-dimensional track and the simulated two-dimensional track is regarded as being the difference between simulated projection data and provided projection data, which is minimized for modifying the kinematics model. By modifying the kinematics model such that a difference between the determined two-dimensional track and the simulated two-dimensional track is minimized, the quality of adapting the model to the moving and/or deforming object can be further improved.
It is preferred that the model modification unit is adapted to
  reconstruct an image of the object from the determined two-dimensional track in the provided projection data,
  arrange the kinematics model such that at least a part of the kinematics model is aligned with a corresponding part of the object shown in the image,
  determine initial kinematics parameters such that a difference between the object shown in the image and the model is minimized,
  modify the model by modifying the initial kinematics parameters such that a difference between the determined two-dimensional track and the simulated two-dimensional track is minimized. A part of a kinematics model or the entire kinematics model can be arranged such that the part or the entire kinematics model is aligned with the corresponding part or the entire object shown in the image. Preferentially, if the object is a catheter, a first, in particular, straight, part of the catheter shown in the image is aligned with a corresponding first part of the kinematics model. The arrangement of the kinematics model such that at least a part of the kinematics model is aligned with a corresponding part of the object shown in the image includes preferentially a rotation and/or a translation of the model. The reconstruction of the image of the object from the determined two-dimensional track in the provided projection data for providing an image, which can be used for the arranging procedure, does preferentially not consider the movement and/or deformation of the object and can therefore be regarded as a rigid reconstruction. This rigid reconstruction leads preferentially to a three-dimensional image of the object, which is used for initially arranging the kinematics model such that at least a part of the kinematics model is aligned with a corresponding part of the object shown in the three-dimensional image. The initialization procedure allows a faster determination of kinematics parameters, which describe the actual location and deformation of the object.

The model modification unit can be adapted to determine one or several two-dimensional tracks or projections of the object in the provided projection data and to determine the simulated projection data such that the simulated projection data define one or several simulated two-dimensional tracks. Accordingly, the model modification unit can be adapted to reconstruct an image for the above described arranging procedure from one or several determined two-dimensional tracks in the provided projection data and to modify the model such that a difference between the determined one or several two-dimensional tracks and the simulated one or several two-dimensional tracks is minimized.

It is further preferred that the object is a first object inserted into a second object, wherein the imaging apparatus comprises an image providing unit for providing an image of the second object and a display for showing the modified model overlaid with the image of the second object. The image of the second object can be a two-, three- or four-dimensional image. The image of the second object can be a fluoroscopy image. It is preferred that the display is adapted to indicate a three-dimensional location of the first object depending on the modified model. For example, the model can be three-dimensionally rendered on the display, in particular, color coding and/or shading can be used for generating a three-dimensional impression of the model. The first object is preferentially a catheter inserted into a person or an animal being the second object. By overlaying the modified model with the image of the second object, the location, in particular, the depth position within the second object, of the first object can be visualized.

The image providing unit is preferentially the above mentioned projection acquisition unit for acquiring, for example, two-dimensional fluoroscopy images. However, the image providing unit can also be another unit for providing another image of the second object like a computed tomography unit, a magnetic resonance imaging unit, a nuclear imaging unit like a single photon emission computed tomography unit or a positron emission tomography unit, an ultrasound imaging unit, or another imaging modality.

It is further preferred that the model providing unit is adapted to store several models corresponding to several objects and to provide a model of the several models, which corresponds to the object to be imaged. A user interface can be provided, in order to allow a person to select a model which corresponds to an actual object to be imaged. The model providing unit can also be adapted to automatically detect the actual object and to provide the corresponding stored model. For example, a rigid reconstruction can be performed based on the projection data acquired in different projection directions, i.e. a three-dimensional image of the object can be reconstructed, wherein it is assumed that the object is not moved and not deformed, and the three-dimensional image can be compared with the stored models, in order to automatically select the model, which corresponds to the object. In another embodiment, a two-dimensional projection image, in particular, a two-dimensional fluoroscopy image, can be compared with simulated projections of the stored models, in order to automatically select the model, which corresponds to the object.

In a further aspect of the present invention an imaging method for imaging an object is presented, wherein the imaging method comprises:
  providing a kinematics model of a robot representing the object, wherein the kinematics model is defined by kinematics parameters,
  providing projection data of the object, which correspond to different projection directions,
  modifying the model by modifying the kinematics parameters such that a difference between simulated projection data, which are determined by simulating a forward projection of the model, and the provided projection data is minimized.

In another aspect of the present invention an imaging computer program for imaging an object is presented, wherein the imaging computer program comprises program code means for causing an imaging apparatus as defined in claim 1 to carry out the steps of the imaging method as defined in claim 11, when the imaging computer program is run on a computer controlling the imaging apparatus.

It shall be understood that the imaging apparatus of claim 1, the imaging method of claim 11 and the imaging computer program of claim 12 have similar and/or identical preferred embodiments as defined in the dependent claims.

It shall be understood that a preferred embodiment of the invention can also be any combination of the dependent claims with the respective independent claim.

These and other aspects of the invention will be apparent from and elucidated with reference to the embodiments described hereinafter.

DETAILED DESCRIPTION OF EMBODIMENTS

Figure 1:
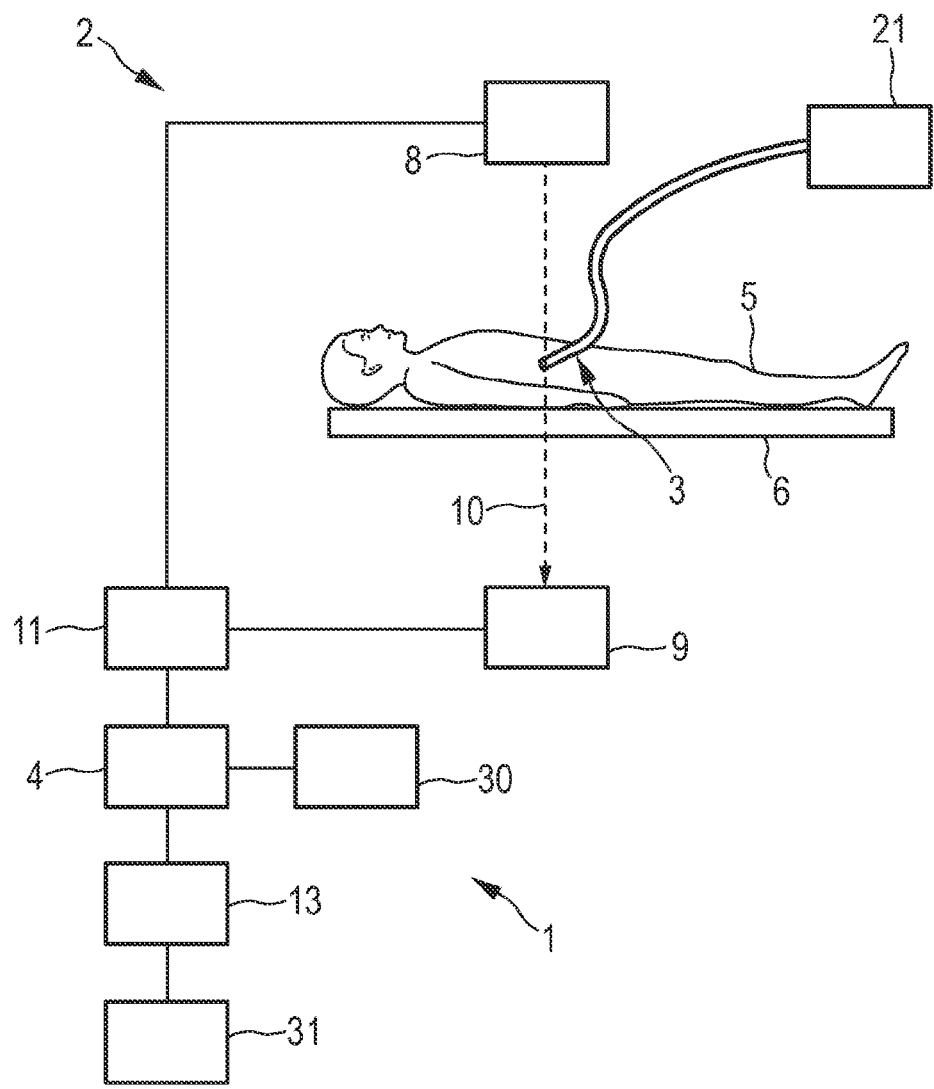
FIG. 1 shows schematically and exemplarily an embodiment of an imaging apparatus for imaging an object.

FIG. 1 shows schematically and exemplarily an embodiment of an imaging apparatus for imaging an object. The imaging apparatus 1 comprises a projection data providing unit 2 for providing projection data of the object 3, which correspond to different projection directions. The imaging apparatus 1 further comprises a model providing unit 4 for providing a kinematics model of a robot representing the object 3, wherein the kinematics model is defined by kinematics parameters, and a model modification unit 13 for modifying the kinematics model by modifying the kinematics parameters such that a difference between simulated projection data, which are determined by simulating a forward projection of the kinematics model, and the provided projection data is minimized. The imaging apparatus 1 further comprises a display 31 for showing an image of the modified model.

The projection data providing unit 2 is preferably a projection acquisition unit comprising a radiation source 8 for emitting radiation 10 for traversing the object 3 and a detection unit 9 for detecting the radiation after having traversed the object 3 and for generating the projection data depending on the detected radiation. In particular, the radiation source 8 is an x-ray source and the detection unit 9 is an x-ray detector. The radiation source 8 and the detection unit 9 can be mounted on a C-arm, of which the angular orientation with respect to the object 3 can be modified, in order to acquire projection data of the object 3, which correspond to different projection directions. The projection acquisition unit further comprises an acquisition control unit 11 for controlling the acquisition of the projection data, in particular, for controlling the movement of the radiation source 8 and the detection unit 9 with respect to the object 3. A C-arm is a well known moveable device, wherein at the ends of the C-arm the radiation source 8 and the detection unit 9 are preferably mounted. The C-arm can be adapted to be rotated about one or more rotational axes. These rotations can be performed by hand or by one or several motors, which can be controlled by the acquisition control unit 11. In this embodiment, the acquisition control unit 11 controls the radiation source 8 and the detection unit 9, in particular, the C-arm on which the radiation source 8 and the detection unit 9 are mounted, such that the radiation source 8 and the detection unit 9 perform a wiggling motion which corresponds to a wiggling of the projection direction. The wiggling is preferably performed by rotating the radiation source 8 and the detection unit 9 around a rotational axis such that an imaginary axis connecting the radiation source 8 and the detection unit 9 traces a surface of an imaginary cone. The imaginary cone has its apex preferably at the isocenter of the rotation. The base of the cone has preferably a circular or elliptical planar shape. The projection data, i.e. a series of two-dimensional projection images, are acquired during the wiggling motion of the radiation source 8 and the detection unit 9.

The object 3 is, in this embodiment, a catheter 3 being inserted into a person 5 who is located on a table 6. The catheter 3 is controlled by a catheter control unit 21. The catheter 3 can be any catheter which can be used in interventional procedures like, for example, an ablation catheter for performing ablation procedures in the heart of the person 5. The catheter control unit 21 is preferentially adapted to allow a user like a physician to control the catheter 3, in particular, to move the catheter 3 into and within the person 5 and to deform the catheter 3. For example, the catheter 3 can comprise pull wires, which can be controlled by the catheter control unit 21 in a known way, in order to move and, in particular, deform the catheter 3.

The model providing unit 4 is preferably adapted to provide a kinematics model of a robot being a continuum robot. Such a kinematics model is schematically and exemplarily represented by links and joints shown in FIG. 2.

The kinematics model 12 comprises a series of rigid links connected by joints 14 . . . 20, wherein each joint describes either a three-dimensional rotation around an axis or a translation along the axis. The respective joint is therefore either a revolute joint 15, 16, 18, 19 or a prismatic joint 14, 17, 20. Each joint can therefore be controlled by a rotation angle $\theta_2$, $\theta_3$, $\theta_5$, $\theta_6$ and a translation distance $d_1$, $d_4$, $d_7$. The kinematics model 12 is defined by a succession of these joints. In particular, the catheter 3, which is preferentially a bidirectional catheter, is modeled by the kinematics model 12 as a succession of joints and links.

Figure 2:
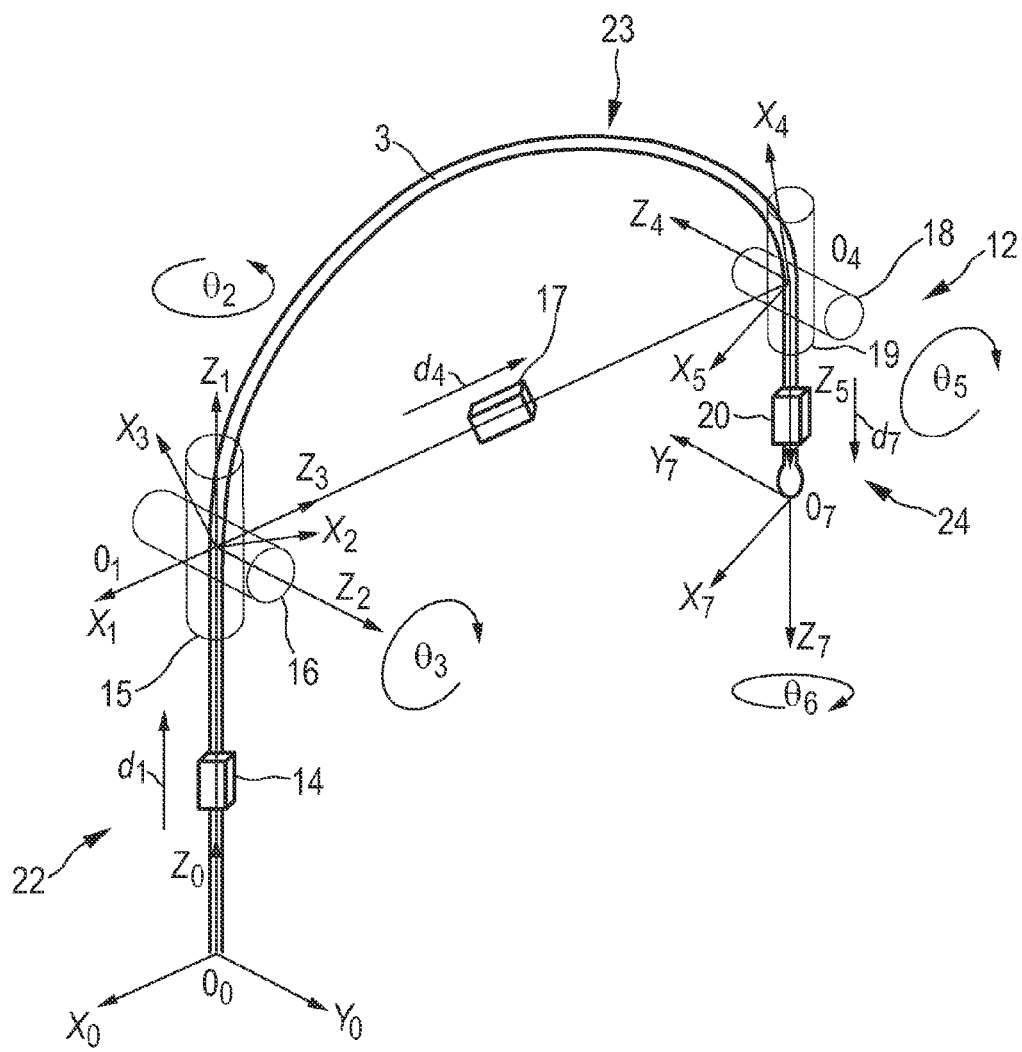
FIG. 2 shows schematically and exemplarily a representation of a kinematics model of a robot representing the object.

In FIG. 2, there are eight links $O_0$ . . . $O_7$, which are connected by each of the joints 14 . . . 20, respectively. In this exemplarily embodiment, the succession of joints and links can be described as follows. The link $O_0$ is connected to the link $O_1$ by the prismatic joint 14 with the kinematics parameter $d_1$. The link $O_1$ is connected to $O_2$ by the revolute joint 15 with the kinematics parameter $\theta_2$, wherein $O_2$ coincides with $O_1$. The link $O_2$ is connected to the link $O_3$ by the revolute joint 16 with the kinematics parameter $\theta_3$, wherein $O_3$ coincides with $O_2$. Moreover, the link $O_3$ is connected to the link $O_4$ by the prismatic joint 17 with the kinematic parameter $d_4$, and the link $O_4$ is connected to the link $O_5$ by the revolute joint 18 with the kinematics parameter $\theta_5$, wherein $O_5$ coincides with $O_4$. The link $O_5$ is connected to the link $O_6$ by the revolute joint 19 with the kinematics parameter $\theta_6$, wherein $O_6$ coincides with $O_5$, and the link $O_6$ is connected to the link $O_7$ by the prismatic joint 20 with the kinematics parameter $d_7$.

The kinematics model further comprises a circular arc, which is not shown in FIG. 2, defined by the chord length $d_4$ between the links $O_4$ and $O_5$. Each joint has its own local coordinate system $X_i$, $Y_i$, $Z_i$, defined according to the D-H convention with respect to the coordinate system of the previous joint, such that i) the z-axis is in the direction of the joint axis; and ii) the x-axis is parallel to the common normal. If there is no unique common normal, then the D-H parameter d is a free parameter and the direction of the x-axis of the current ordinate system points from a z-position of the previous z-axis to the corresponding z-position of the current z-axis. The y-axis follows from the x-and z-axis by choosing it to be a right-handed coordinate system. Each coordinate system thus refers to the next joint, i.e. $X_i$, $Y_i$, $Z_i$ centered at $O_1$ refers to joint i+1. In particular, $O_0$ is the coordinate center, i.e. origin, for the prismatic joint with parameter $d_1$, $O_1$ refers to $\theta_2$, $O_2$ refers to $\theta_3$, et cetera.

It should be noted that FIG. 2 does not show the entire kinematics model 12, but only a schematic representation, in which the joints 14 . . . 20 are emphasized and the links $O_0$ . . . $O_7$.

Figures 3, 4:
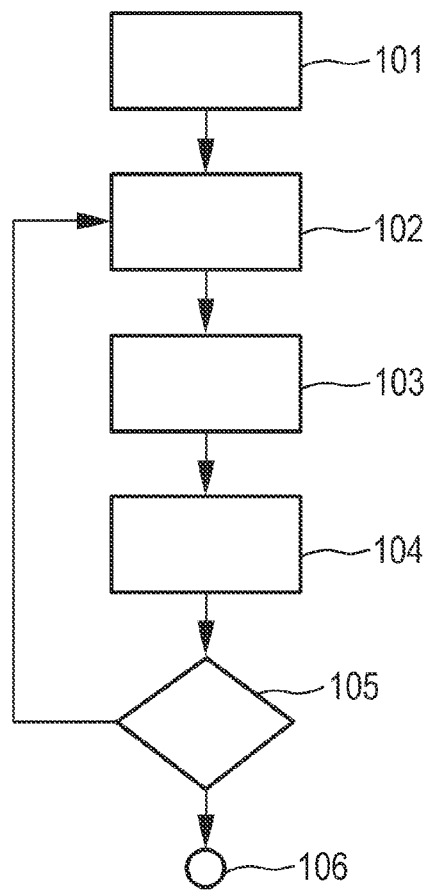
FIG. 3 shows exemplarily a table of kinematics parameters of the kinematics model.
FIG. 4 shows a flowchart exemplarily illustrating an embodiment of an imaging method for imaging an object.

The kinematics model 12 with the models the kinematics of the steerable bidirectional catheter 3, in particular, the bending properties of the catheter 3 as controlled by pull wires, which are located within the catheter 3 and which can be controlled via the catheter control unit 21. The kinematics model 12 is defined by the succession of joints, which can be represented by TRRTRRT, wherein T indicates a translation and R indicates a rotation. The kinematics model 12 comprises three sections. A virtual base 22 of a distal shaft of the catheter 3, represented by a prismatic joint 14, a bending section 23 of the distal shaft of the catheter 3, represented by two rotations, in particular twist and deflection, followed by a translation and two more rotations, and a distal end 24 of the catheter 3, which has a fixed length and is almost rigid. The distal end is also represented by a prismatic joint with fixed translation. The corresponding pose of each joint is preferentially represented by four kinematics parameters in the D-H convention, which are schematically and exemplarily shown in FIG. 3. In FIG. 3, the first column indicated by "L" indicates different links.

In FIG. 2, as already mentioned above, the links are conceptually represented by the points $O_0 \ldots O_7$. The kinematic parameters of the table shown in FIG. 3 describe the transformation between the local coordinate system of one link to the local coordinate system of the previous link, wherein it is started at $O_0$. In particular, the kinematics parameters, i.e., in this embodiment, the D-H parameters, have the following meaning: d denotes the offset along the previous z-axis to the common normal; θ denotes the angle about the previous z-axis from the old x-axis to the new x-axis; a denotes the length of the common normal, assuming a revolute joint, being the radius about the previous z-axis; and α is the angle about the common normal from the previous z-axis to the current z-axis. For more details concerning the D-H parameter reference is made to "Robotics—Modelling, Planning and Control" by B. Siciliano et al., pages 58-65, Springer Verlag London, 2009.

The pose of each joint and, thus, the configuration of the kinematics model can therefore be described by the D-H parameters.

It is assumed that, because of the pull wire mechanism, the deflection of the catheter 3 is in-plane, i.e. that the catheter 3 bends with zero-torsion, and that the bending occurs with constant curvature such that the distal shaft takes the shape of a circular arc. Because of this assumption, the second pair of rotations in the bending section 23 is coupled to the first two rotations. Additionally, since the total arc length of the bending section 23 is fixed, the length of the prismatic joint between the two pairs of rotations is entirely controlled by the deflection angle $\theta_3$. It follows that the total number of free kinematics parameters for the kinematics model 12 is three. The model modification unit 13 is therefore preferentially adapted to modify the kinematics model 12 by modifying the three free kinematics parameters $d_1, \theta_2, \theta_3$.

In particular, the model modification unit 13 is adapted to determine two-dimensional tracks of projections of the catheter 3 in the provided projection data. Since the radiation source 8 and the detection unit 9 perform a wiggling motion while acquiring the projection data, the projection of the catheter 3 moves along two-dimensional tracks. The two-dimensional tracks can be determined by segmenting the projection of the catheter 3 in the projection data, which are two-dimensional projection images. For segmenting the projection of the catheter 3 in a two-dimensional projection image known segmentation methods can be used like region growing, thresholding, et cetera. After the projection of the catheter 3 has been segmented in the two-dimensional projection images, the position of the segmented projection of the catheter 3 can be determined based on the projection geometry in each of the two-dimensional projection images, wherein the determined positions of the projection of the catheter 3 in the two-dimensional projection images define the two-dimensional tracks. The model modification unit 13 is further adapted to reconstruct a three-dimensional image of the catheter 3 from the determined two-dimensional tracks. In other words, the projection data, which correspond to different projection directions, can be used for reconstructing a three-dimensional image of the catheter. For example, the projection data can simply be backprojected, in order to reconstruct the three-dimensional image, by using the determined two-dimensional tracks and the known projection geometry. The three-dimensional image has a reduced quality, because the projection data have been acquired over only a relatively small angular range, but the reduced quality is sufficient for aligning the kinematics model. The model modification unit 13 is further adapted to then arrange the kinematics model 12 such that at least a part of the kinematics model is aligned with a corresponding part of the catheter 3 shown in the reconstructed three-dimensional image, which has been reconstructed as if the catheter 3 were static, i.e. which has been rigidly reconstructed. In particular, the model modification unit 13 is adapted to calculate a three-dimensional transformation, which preferentially includes a rotation and a translation, to match the first part of the catheter 3, which is preferentially substantially straight, to the corresponding first part of the kinematics model 12 between $O_0$ and $O_1$ in FIG. 2. Thus, the kinematics model 12 of the catheter 3 is rotated and translated to match the rigid reconstruction. Initially, by convention the first part of the kinematics model is preferentially placed parallel to the z-axis of the coordinate system at $O_0$.

The model modification unit 13 is further adapted to determine initial kinematics parameters such that a difference between the catheter 3 shown in the three-dimensional image and the kinematics model 12 including the circular arc defined by the chord length $d_4$ is minimized. Thus, the overall orientation and position of the kinematics model 12 is determined by the three-dimensional transformation such that the kinematics model 12 matches the reconstructed three-dimensional image of the object as good as possible, and then the kinematics parameters are modified, in order to modify the shape or deformation of the kinematics model 12, such that a difference between the catheter 3 shown in the three-dimensional image and the kinematics model 12 is minimized, thereby determining the initial kinematics parameters. In this embodiment, the initial kinematics parameters are parameters in the D-H convention, wherein each joint is characterized by four kinematics parameters. These initial kinematics parameters that best explain the rigid reconstruction are preferentially determined by using inverse kinematics. Inverse kinematics is a known method to get robotics model parameters given the three-dimensional posture or three-dimensional shape of an object. Posture means preferentially the three-dimensional position and orientation of each of the links comprising the object. In this embodiment, the initial kinematics parameters are determined by solving following non-linear optimization problem:

$$\hat{p}^R = \arg\min \sum_{j=1}^{N} \|X_j^R - S_j^R(p^R)\|^2. \tag{1}$$

In equation (1), the superscript R indicates that during solving the non-linear problem in accordance with equation (1) it is assumed that the object is rigid. The three-dimensional reconstructed image of the object, which is based on the measured two-dimensional tracks, is denoted by $X_j^R$, wherein j indicates different sample points or voxels of the object shown in the three-dimensional image. In particular, $X_j^R$ denotes the three-dimensional position of the sample point indicated by j. The variable N denotes the number of sample points or voxels of the three-dimensional reconstruction of the object, and $S^R(p^R)$ denotes the three-dimensional model in the respective pose as a function of the kinematics parameters $p^R$. Preferentially, the model including the circular arc defined by the chord length $d_4$ is sampled by N sample points along the length of the model representing the catheter, in particular, from $O_0$ or $O_1$ to $O_7$, wherein the sampling intervals can be equidistant. The sampling is, of course, similarly performed with respect to the reconstructed object, in order to allow solving equation (1).

The model modification unit 13 can be adapted to solve the non-linear optimization problem in accordance with equation (1) by using a free inverse kinematics solver as published, for example, in the article "A Robotics Toolbox for MATLAB" by P.I. Corke, IEEE Robotics and Automation Magazine, Vol. 3, pp.24-32, March 1996.

The solution of the non-linear optimization problem in accordance with equation (1) provides initial kinematics parameters which result from the rigid reconstruction of the catheter 3. The initialization consists therefore of firstly making a rigid reconstruction of the catheter 3 by using the determined two-dimensional tracks, wherein the rigid reconstruction, i.e. the rigidly reconstructed image of the catheter 3, represents the correct solution, if the object had not moved. From this rigid reconstruction the initial kinematics parameters are obtained using inverse kinematics, i.e., for example, by solving the non-linear optimization problem in accordance with equation (1).

Since during initialization the kinematics model 12 has been arranged such that at least a part of the kinematics model is aligned with a corresponding part of the object shown in the image, in particular, since the kinematics model 12 has been arranged such that the first part 22 of the kinematics model matches the corresponding first straight part of the catheter 3, the overall position and orientation of the kinematics model 12 is already aligned with the catheter 3. In order to describe a deformation of the catheter 3, only the above mentioned three free kinematics parameters $d_1, \theta_2, \theta_3$ have to be modified. Initially, these free kinematics parameters are determined by solving the non-linear optimization problem in accordance with equation (1), in order to determine the initial kinematics parameters. The kinematics parameters $d_1, \theta_2, \theta_3$ are the only free kinematics parameters of the bidirectional catheter 3, because a) $\theta_5$ is coupled with $\theta_3$, and $\theta_6$ is coupled with $\theta_2$, b) $d_4$ is a known function of $\theta_3$ and L being the fixed length of the distal shaft of the bidirectional catheter 3, and c) $d_7$ is fixed and known for the catheter 3.

The model modification unit 13 is further adapted to determine the simulated projection data such that the simulated projection data define simulated two-dimensional tracks by forward projecting the kinematics model 12 including the circular arc defined by the chord length $d_4$ and to modify the initial kinematics parameters, in particular, the three free initial kinematics parameters $d_1, \theta_2, \theta_3$, such that a difference between the determined two-dimensional tracks, which have been determined from the measured projection data, i.e. from the acquired two-dimensional images, and the simulated two-dimensional tracks is minimized. Thus, a re-projection error is minimized, in order to determine optimized kinematics parameters, which describe for each projection direction, i.e. for each point in time or frame, the deformation of the catheter 3. The re-projection error is preferentially minimized by solving an optimization problem in accordance with following equation:

$$\hat{p} = \arg\min \sum_{i,j}^{F,N} \|x_{ij} - \hat{x}_{ij}\|^2, \quad (2)$$

wherein $$\hat{x}_i \propto P_i S_i(p_i). \quad (3)$$

In equation (2), $\hat{p}$ denotes the resulting optimized kinematics parameters $d_1, \theta_2, \theta_3$, F denotes the number of frames, i.e. the number of acquired projections, wherein i=1 ... F, and $x_{ij}$ denotes the tracked points, i.e. the two-dimensional positions of the tracked points. The corresponding simulated values are denoted by $\hat{x}_{ij}$. In equation (3), is an N-dimensional vector comprising the values $\hat{x}_{ij}$, $P_i$ denotes the forward-projection matrix for the frame denoted by i and $S_i(p_i)$ denotes the three-dimensional shape, i.e. the posture, of the kinematics model as function of the kinematics parameters $p_i = (d_1^i, \theta_2^i, \theta_3^i)$ for the respective frame denoted by i. In particular, for each sample point, which is indicated by j, of the kinematics model with the three-dimensional shape $S_i(p_i)$ and for each projection, which is indicated by i, a single simulated track position $\hat{x}_{ij}$ is determined by using the forward-projection matrix $P_i$. The two-dimensional tracks determined from the measured projections is sampled in accordance with the sampling of the simulated track position values $\hat{x}_{ij}$, in order to allow using equation (2).

The model modification unit can be adapted to perform the calculations in accordance with at least equations (2) and (3) in homogeneous coordinates as defined in, for example, the book "Multiple View Geometry in Computer Vision", Richard Hartley et al., pages 1-9, Cambridge University Press, 2004.

The model modification unit 13 is adapted to solve the optimization problem in accordance with equation (2), in order to determine the kinematics parameters $d_1, \theta_2, \theta_3$ for the current deformation of the catheter 3. For example, the model modification unit 13 can be adapted to iteratively solve the optimization problem. For example, the known Levenberg-Marquardt algorithm (LMA) can be used for solving the optimization problem. The LMA interpolates between the Gauss-Newton algorithm (GNA) and a gradient descent. Also other known algorithms can be used for solving the optimization problem in accordance with equation (2), i.e. for minimizing the difference between the simulated projection data and the acquired projection data. For instance, gradient descent, Gauss-Newton, trust-region, quadratic programming et cetera algorithms can be used for determining the kinematics parameters $d_1, \theta_2, \theta_3$ in accordance with equation (2).

The display 31 is adapted to show the modified kinematics model 12 overlaid with an image of the person 5. In this embodiment, the projection acquisition unit 2 generates two-dimensional fluoroscopy images, which are used for modifying the kinematics model 12, while the catheter 3 is deformed and which are shown on the display 31 overlaid with the modified kinematics model 12. In particular, the kinematics model 12 is modified in real-time in accordance with a deformation of the catheter 3 and the deformation is shown in real-time on the display 31 by overlaying an image of the kinematics model 12, which is modified in real-time, with the two-dimensional fluoroscopy image. For example, the kinematics model can be three-dimensionally rendered on the display 31, in particular, color coding and/or shading can be used for generating a three-dimensional impression of the kinematics model. The color coding can also be used to color the model with different colors depending on the respective depths, for example, with respect to the distance of the respective part of the model to the detection unit. In an embodiment, parts of the model being close to the detection unit can be colored by a first color, for example, by red, and parts of the model being close to the radiation source can be colored by a second color, for example, by blue, wherein the parts of the object between the first color and the second color can be colored in varying shades depending on their respective distance to the detection unit and the radiation source. In another embodiment, instead of overlaying the image of the modified kinematics model with the two-dimensional fluoroscopy image, the image of the modified kinematics model can also be overlaid with another image of the person 5, in particular, a two-, three- or four-dimensional image of the person 5. The image of the person 5 can be an image, which has been acquired by another imaging modality like a computed tomography apparatus, a magnetic resonance imaging apparatus or a nuclear imaging apparatus, for example, a single photon emission computed tomography apparatus or a positron emission tomography apparatus. In the present embodiment, the image of the person 5 is provided by the projection acquisition unit 2, which can therefore be regarded as being an image providing unit. In another embodiment, the imaging providing unit can be a storage unit, in which an already acquired image of the person 5 is stored.

The display 31 can comprise a two-dimensional or a three-dimensional screen.

Although in the above described embodiments the model modification unit is adapted to modify only the free three kinematics parameters $d_1, \theta_2, \theta_3$, the model modification unit can also be adapted to modify more than three kinematics parameters and/or calibration parameters. In particular, the model modification unit can be adapted to modify the calibration parameters and the kinematics parameters such that a difference between simulated projection data, which are determined by simulating a forward projection of the model, and the provided projection data is minimized. The calibration parameters preferentially define which projection data value detected by the detection unit corresponds to which beam direction, i.e. corresponds to which direction along the beam has travelled, which has met the detection unit at the respective detection location at which the respective projection data value has been detected. The calibration parameters describe therefore preferentially the projection geometry. The calibration parameters can be intrinsic calibration parameters or extrinsic calibration parameters.

The model providing unit 4 is adapted to store several models corresponding to several objects and to provide a kinematics model of the several models, which corresponds to the object to be imaged. Thus, the object to be imaged does not need to be the above described bidirectional catheter. The object to be imaged can also be another object like another catheter, a needle, et cetera, wherein the model providing unit 4 provides the kinematics model, which corresponds to the actual object to be imaged. In this embodiment, a user interface 30 is provided for allowing a user to select a model which corresponds to the actual object to be imaged. The model providing unit can also be adapted to automatically detect the actual object and to provide the corresponding stored model. For example, the above described rigid reconstruction of a three-dimensional image of the object can be performed, wherein it is assumed that the object is not moved and not deformed, and the three-dimensional image can be compared with the stored models, in order to automatically select the model, which corresponds to the object. In a further embodiment, a two-dimensional projection image, in particular, a two-dimensional fluoroscopy image, can be compared with simulated projections of the stored models, in order to automatically select the model, which corresponds to the object. Each object can be modeled beforehand such that the links and joints, the kinematics parameters, in particular, the free kinematics parameters after the overall model has been arranged based on the rigid reconstruction, and possible value ranges of the kinematics parameters are predefined. Since surgical instruments are typically well described and can be obtained beforehand, it is easy to perform off-line tests in a lab to determine the best formulation for each application, for example, for catheter ablation, valve replacement, et cetera.

Also for other objects not being surgical instruments the links and joints of the kinematics model of a robot and the corresponding kinematics parameters can be determined beforehand.

In the following an embodiment of an imaging method for imaging an object will exemplarily be described with reference to a flowchart shown in FIG. 4.

In step 101, a user can select a kinematics model of a robot representing the object, wherein the kinematics model is defined by kinematics parameters, by using the user interface 30. The user selects, for example, the above described kinematics model of the bidirectional catheter 3.

In step 102, projection data of the object are provided, which correspond to different projection directions. In this embodiment, the projection acquisition unit 2 acquires projection data, i.e. several two-dimensional projection images, while the radiation source 8 and the detection unit 9 perform a wiggling motion and while the object, which is, in this embodiment, a bidirectional catheter 3, is deformed. In step 103, the selected kinematics model 12 is modified by modifying the kinematics parameters such that a difference between simulated projection data, which are determined by simulating a forward projection of the model, and the provided projection data is minimized. Preferentially, the kinematics parameters are initialized by performing a rigid reconstruction based on the provided projection data, which is a reconstruction which does not consider the deformation of the object, as described above. In step 104, the modified kinematics model is shown on the display 31 overlaid with the two-dimensional projection images, which form preferentially a two-dimensional fluoroscopy image, acquired by the projection acquisition unit 2. In step 105, it is decided whether an abort criterion has been fulfilled or not. If the abort criterion has not been fulfilled, the method continuous with step 102, and, if the abort criterion has been fulfilled, the method ends in step 106. The abort criterion is, for example, whether a person has indicated, for example, by using a user interface, that the imaging method should be stopped. Or, the abort criterion can be fulfilled, if the acquisition time has exceeded a predefined threshold.

Interventional radiology provides an option for minimally invasive diagnosis and treatment of many conditions in the field of cardiology, neurology and endovascular medicine, minimally invasive procedures are typically performed under fluoroscopic x-ray guidance to assist in the navigation of surgical instruments in the anatomy. To support the intervention it can be useful to get detailed information about the three-dimensional position and orientation of the surgical instrument during its guidance. Such instruments can include catheters, needles, et cetera. The above described imaging apparatus and imaging method can be used to create and display live three-dimensional information on such instruments using multiple x-ray views created by a wiggle acquisition. The imaging apparatus and imaging method are preferentially adapted to perform the imaging of the object, in particular, to retrieve depth information defining the depth position within a person or an animal, using only the two-dimensional life image data, i.e. fluoroscopy projection data.

Although in the above described embodiments the radiation source and the detection unit are both moved, for example, by moving a C-arm on which they are mounted, in order to perform the wiggle movement, it is also possible that the radiation source is moved with respect to the detection unit or vice versa.

Although in the above described embodiments a catheter has been described as the object to be imaged, which is inserted into a person, also other objects can be imaged which can be inserted into, for example, a technical object, which is not a person, or the object to be imaged can be inserted in an animal.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

The calculations like the rigid reconstruction, the determination of the initial kinematics parameters, the modification of the kinematics parameters, et cetera performed by one or several units or devices can be performed by any other number of units or devices. The calculations and/or the control of the imaging apparatus in accordance with the imaging method can be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention relates to an imaging apparatus for imaging an object being preferentially a catheter. A kinematics model of a robot representing the object, which is defined by kinematics parameters, and projection data of the object, which correspond to different projection directions, are provided. The kinematics model is modified by modifying the kinematics parameters such that a difference between simulated projection data, which are determined by simulating a forward projection of the kinematics model, and the provided projection data is minimized. Since the object is represented by a kinematics model of a robot, movements of the object, in particular, deformations of the object, can be described in a simple way by few kinematics parameters, thereby allowing modifying the model and, thus, following a movement of the object fast by modifying the few kinematics parameters, in particular, in real-time.

The invention claimed is:

1. An imaging apparatus for imaging an object, the imaging apparatus (1) comprising:
a model providing unit (4) for providing a kinematics model (12) of a robot representing the object (3), wherein the kinematics model (12) is defined by kinematics parameters,
a projection data providing unit (2) for providing projection data of the object (3), which correspond to different projection directions,
a model modification unit (13) for modifying the kinematics model (12) by modifying the kinematics parameters such that a difference between simulated projection data, which are determined by simulating a forward projection of the kinematics model, and the provided projection data is minimized.

2. The imaging apparatus as defined in claim 1, wherein the projection data providing unit (2) is adapted to provide projection data which correspond to a wiggling of the projection direction.

3. The imaging apparatus as defined in claim 1, wherein the projection data represent projections generated by using a projection acquisition unit (2), wherein a calibration of the projection acquisition unit (2) is defined by calibration parameters, and wherein the model modification unit (13) is adapted to modify the calibration parameters and the kinematics parameters such that a difference between simulated projection data, which are determined by simulating a forward projection of the model, and the provided projection data is minimized.

4. The imaging apparatus as defined in claim 1, wherein the kinematics model (12) comprises a series of rigid links connected by joints (14 . . . 20), wherein each joint describes either a three-dimensional rotation around an axis or a translation along the axis.

5. The imaging apparatus as defined in claim 4, wherein the object (3) is a catheter and the kinematics model (12) comprises seven joints which are controlled by three kinematics parameters ($d_1$, $\theta_2$, $\theta_3$), wherein the model modification unit (13) is adapted to modify the model (12) by modifying the three kinematics parameters ($d_1$, $\theta_2$, $\theta_3$).

6. The imaging apparatus as defined in claim 1, wherein the model modification unit (13) is adapted to
determine a two-dimensional track of projections of the object (3) in the provided projection data,
determine the simulated projection data such that the simulated projection data define a simulated two-dimensional track,
modify the model such that a difference between the determined two-dimensional track and the simulated two-dimensional track is minimized.

7. The imaging apparatus as defined in claim 6, wherein the model modification unit (13) is adapted to
reconstruct an image of the object (3) from the determined two-dimensional tracks in the provided projection data,
arrange the kinematics model such that at least a part of the kinematics model is aligned with a corresponding part of the object (3) shown in the image,
determine initial kinematics parameters such that a difference between the object (3) shown in the image and the model (12) is minimized,
modify the model (12) by modifying the initial kinematics parameters such that a difference between the determined two-dimensional track and the simulated two-dimensional track is minimized.

8. The imaging apparatus as defined in claim 1, wherein the object is a first object (3) inserted into a second object (5), wherein the imaging apparatus (1) comprises an image providing unit for providing an image of the second object (5) and a display (31) for showing the modified model overlaid with the image of the second object (5).

9. The imaging apparatus as defined in claim 8, wherein the display (31) is adapted to indicate a three-dimensional location of the first object (3) depending on the modified model (12).

10. The imaging apparatus as defined in claim 1, wherein the model providing unit (4) is adapted to store several models corresponding to several objects and to provide a model (12) of the several models, which corresponds to the object (3) to be imaged.

11. An imaging method for imaging an object, the imaging method comprising:
providing a kinematics model (12) of a robot representing the object (3), wherein the kinematics model (12) is defined by kinematics parameters,
providing projection data of the object (3), which correspond to different projection directions, modifying the model (12) by modifying the kinematics parameters such that a difference between simulated projection data, which are determined by simulating a forward projection of the model, and the provided projection data is minimized.

12. An imaging computer program for imaging an object, the imaging computer program comprising program code means for causing an imaging apparatus as defined in claim 1.

* * * * *